United States Patent [19]

Hakamatsuka et al.

[11] Patent Number: 5,156,623
[45] Date of Patent: Oct. 20, 1992

[54] SUSTAINED RELEASE MATERIAL AND METHOD OF MANUFACTURING THE SAME

[75] Inventors: Yasuharu Hakamatsuka, Akishima; Hiroyuki Irie, Hachioji, both of Japan

[73] Assignee: Olympus Optical Co., Ltd., Tokyo, Japan

[21] Appl. No.: 681,084

[22] Filed: Apr. 5, 1991

[30] Foreign Application Priority Data

Apr. 16, 1990 [JP] Japan .................................. 2-99642
Apr. 16, 1990 [JP] Japan .................................. 2-99643

[51] Int. Cl.⁵ .............................................. A61F 2/02
[52] U.S. Cl. ............................ 623/11; 604/890.1; 604/891.1
[58] Field of Search ................... 604/890.1, 891.1; 623/11

[56] References Cited

U.S. PATENT DOCUMENTS 4,351,337  9/1982  Sidman ................. 604/891.1
4,455,143  6/1984  Theeuwes et al. ....... 604/890.1
4,655,766  4/1987  Theeuwes et al. ....... 604/891.1
4,955,881  9/1990  Eckenhoff ............. 604/891.1

FOREIGN PATENT DOCUMENTS 2153675  8/1985  United Kingdom ........... 604/890.1
2178660  2/1987  United Kingdom ........... 604/890.1
2179252  3/1987  United Kingdom ........... 604/890.1

Primary Examiner—David J. Isabella
Assistant Examiner—D. S. Brittingham
Attorney, Agent, or Firm—Frishauf, Holtz, Goodman & Woodward

[57] ABSTRACT

A sustained release material to be buried at a position close to a diseased part in a living body to slowly release an impregnated liquid drug includes a core mainly consisting of a ceramic material and having a plurality of pores formed at a predetermined porosity, and a surface layer mainly consisting of a ceramic material, formed around the outer surface of the core, and having a plurality of pores having a pore size or porosity smaller than that of the pores formed in the core.

5 Claims, 3 Drawing Sheets

" "# SUSTAINED RELEASE MATERIAL AND METHOD OF MANUFACTURING THE SAME

BACKGROUND OF THE INVENTION

1. Field of the Invention

The present invention relates to a sustained release material which is buried at a position near to a diseased part in a living body in order to cure the diseased part inside the living body and slowly releases a liquid drug such as an antibiotics or an anticancer agent impregnated in the sustained release material beforehand, and a method of manufacturing the same.

2. Description of the Related Art

To cure osteomyelitis, tumor, cancer, or the like, an antibiotic or an anticancer agent must be administered to a diseased part present in a living body. For this purpose, a sustained release material capable of administering a suitable amount of a drug to only a diseased part in a living body has been developed.

This sustained release material can prevent problems, often observed in whole-body administration, that only a slight amount of the entire dose of a drug has an effect on a diseased part or a side effect of the administration is enhanced.

Published Unexamined Japanese Patent Application Nos. 59-101145 and 61-47401 describe techniques related to the present invention. Published Unexamined Japanese Patent Application No. 59-101145 describes a method in which a liquid drug is impregnated in a porous ceramic and the ceramic is buried in a diseased part to administer a suitable amount of the drug to the diseased part. Published Unexamined Japanese Patent Application No. 61-47401 discloses a sustained release material formed by using calcium phosphate having a large specific surface area as a base material and causing this calcium phosphate to adsorb a drug.

Since, however, the above porous ceramic or sustained release material has only a short release period for slow release of an impregnated drug, no satisfactory therapeutic effect can be obtained.

More specifically, the conventional sustained release material is obtained by causing a base material to be impregnated with or to adsorb a drug and burying it in a diseased part to release the drug, and a porous ceramic is used as the base material for obtaining this effect. However, since only few drugs can be chemically adsorbed in the base material and most drugs are only physically adsorbed therein, release of a drug cannot continue long. Therefore, it is difficult to control slow-releasing characteristics even by changing the pore size or the porosity of the porous ceramic.

SUMMARY OF THE INVENTION

It is an object of the present invention to provide a sustained release material capable of releasing a liquid drug over a long time period and obtaining a satisfactory therapeutic effect.

According to an aspect of the present invention, there is provided a sustained release material to be buried at a position close to a diseased part in a living body to slowly release an impregnated liquid drug, comprising a core mainly including of a ceramic material and having a plurality of pores formed at a predetermined porosity, and a surface layer mainly including of a ceramic material, formed around an outer surface of the core, and having a plurality of pores having a pore size or porosity smaller than that of the pores formed in the core.

According to another aspect of the present invention, there is provided a sustained release material to be buried at a position close to a diseased part in a living body to slowly release an impregnated liquid drug, comprising a first core mainly including of a ceramic material and having a plurality of pores formed at a predetermined porosity, a second core mainly consisting of a ceramic material, bonded to a portion of an outer surface of the first core, and having a plurality of pores having a pore size or porosity smaller than that of the pores formed in the first core, and a dense surface layer formed around outer surfaces of the first and second cores and having a communication port for allowing the second core to communicate with the exterior to externally release the liquid drug.

According to still another aspect of the present invention, there is provided a sustained release material to be buried at a position close to a diseased part in a living body to slowly release an impregnated liquid drug, comprising a porous core into which the liquid drug is impregnated, a dense first interlayer formed around the core, a porous second interlayer formed around the first interlayer, a dense surface layer formed around the second interlayer, a first communication path for allowing the core to communicate with the first interlayer, and a second communication path for allowing the second interlayer to communicate with the exterior.

According to still another aspect of the present invention, there is provided a method of manufacturing a sustained release material, comprising a first step of casting a core slurry prepared by mixing at least a foaming agent, water and a ceramic powder into a predetermined mold to form a core molded body, a second step of filling a surface layer slurry prepared by mixing at least a foaming agent, water and a ceramic powder into a split mold to be divided into two pieces, and performing drying with the core molded body being placed in a central portion of the split mold, thereby forming a surface layer molded body consisting of the surface layer slurry around the core molded body, and a third step of further sintering the core molded body and the surface layer molded body at a predetermined temperature.

According to still another aspect of the present invention, there is provided a method of manufacturing a sustained release material, comprising a first step of casting a first core slurry prepared by adding at least a foaming agent and water to a ceramic powder into a predetermined mold to form a first core molded body, a second step of casting a second core slurry prepared by adding at least a foaming agent and water to a ceramic powder into a predetermined mold to form a second core molded body, a third step of bonding the first and second core molded bodies to each other using a wax and welding a distal end portion of a stick wax to a portion of a surface of the second core molded body, thereby forming a bonded molded body, a fourth step of dipping the bonded molded body into a surface layer slurry prepared by adding at least an aqueous deflocculant solution to a ceramic powder to adhere the surface layer slurry around the bonded molded body, and a fifth step of sintering the bonded molded body on which the surface layer slurry is adhered in the fourth step at a predetermined temperature, thereby forming a dense surface layer molded body consisting of the sintered surface layer slurry around the bonded molded body, forming a first communication port between the first and second core molded bodies upon melting of the wax between the first and second molded bodies, and forming a second communication port for allowing a portion of the second core molded body at which the stick wax is welded to communicate with the exterior upon melting of the stick wax.

According to still another aspect of the present invention, there is provided a method of manufacturing a sustained release material, comprising a first step of casting a foaming slurry prepared by adding at least a foaming agent and water to a ceramic powder into a predetermined mold and drying the foaming slurry to form a core molded body, a second step of adhering a distal end of a stick wax to a surface of the core molded body, adhering a dense slurry prepared by adding at least an aqueous deflocculant solution to a ceramic powder around the core molded body by using the stick wax, drying the adhered dense slurry to form a dense first interlayer molded body around the core molded body, and removing the wax to form a communication path communicating with the core molded body in a portion from which the wax is removed, thereby forming an intermediate molded body, a third step of dipping the intermediate molded body formed in the second step into the foaming slurry to adhere the foaming slurry around the intermediate molded body, and drying the adhered foaming slurry to form a porous second intermediate molded body around the intermediate molded body, and a fourth step of adhering a distal end of a stick wax on a surface of the second interlayer molded body, adhering the dense slurry on the surface of the interlayer molded body by using the stick wax, drying the adhered dense slurry to form a dense surface layer molded body around the second interlayer molded body, and removing the wax to form a communication path communicating with the second interlayer molded body in a portion from which the wax is removed.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE PREFERRED EMBODIMENTS

Embodiments of the present invention will be described below.

Figure 1:
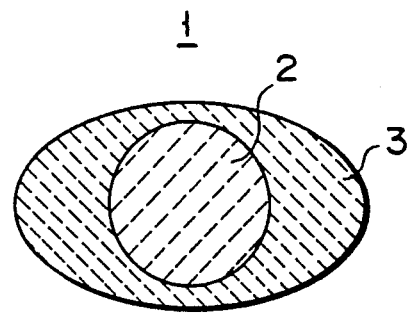
FIG. 1 is a sectional view showing a sustained release material according to the first embodiment of the present invention.

FIG. 1 is a sectional view showing a sustained release material according to the first embodiment of the present invention. This sustained release material 1 has an elliptic shape as a whole. A spherical porous core 2 having a porosity of 70% is arranged at the central portion of the sustained release material 1, and an elliptic porous surface layer 3 having a porosity of 25% is formed around the core 2. The pore size of the core 2 is set to be 500 μm or less, and that of the surface layer 3 is set to be 100 μm or less.

A method of manufacturing the sustained release material 1 will be described below.

In this embodiment, β-tricalcium phosphate (to be referred to as "β-TCP" hereinafter) having high affinity to a living body is used as a base material.

First, 3 ml of a foaming agent, 15 ml of a foam stabilizer, and 15 ml of water are added to 30 g of a β-TCP powder synthesized by a mechanochemical method, and the resultant material is mixed under stirring, thereby preparing a high-porosity foaming slurry (a slurry controlled to achieve a porosity of 70%). This high-porosity slurry is subjected to casting using a silicone rubber mold capable of molding a sphere having a diameter of 5 mm. The molded slurry is left to stand and dried to form a high-porosity dried molded body.

In a separate step, 2 ml of a foaming agent, 5 ml of a foam stabilizer, and 7 ml of water are added to 30 g of a β-TCP powder synthesized by the mechanochemical method and the resultant material is mixed to prepare a low-porosity foaming slurry (a slurry controlled to achieve a porosity of 25%). The prepared low-porosity slurry is molded using an elliptic silicone rubber split mold having a major diameter of 12 mm and a minor diameter of 7 mm. That is, the low-porosity foaming slurry is filled in each piece of the split mold, and the mold are mated (closed) with each other so that the high-porosity dried molded body is located in the central portion of the split mold. The split mold is dried and sintered at 1,100° C. for one hour. As a result, the sustained release material 1 shown in FIG. 1 is obtained.

A liquid drug is impregnated in the obtained sustained release material 1 at a reduced pressure. The sustained release material 1 in which the liquid drug is impregnated in the spherical porous core 2 is buried in a diseased part to slowly release the drug. A release rate at this time is determined by the porosity of the elliptic porous body 3. Since the sustained release material of this embodiment has this elliptic shape, the diffusion and release of the drug is fast in the vertical direction on the paper surface of FIG. 1 and slow in its horizontal direction.

According to the embodiment having the above arrangement, since the elliptic surface layer 3 having a porosity of 25% surrounds the spherical core 2 having a porosity of 70%, the liquid drug can be satisfactorily impregnated in the spherical core 2, and the sustained release period can be controlled by the elliptic surface layer 3. Therefore, as compared with a conventional sustained release material consisting of only a ceramic, the impregnation amount of a liquid drug can be increased to enable sustained release over a long time period, thereby realizing a more satisfactory therapeutic effect.

In addition, since a material having high affinity to a living body such as $\beta$-TCP is used as the base material, after the sustained release material 1 buried in a bone tissue has released a drug, it is bonded well to the bone and changed into a bone as time elapses.

Examples of the material having high affinity to a living body are, in addition to above-mentioned $\beta$-TCP, apatite hydroxide, a composite material of $\beta$-TCP and apatite hydroxide, calcium phosphate, alumina, and zirconia. The same effect as in the above embodiment can be obtained by using any of these materials.

Figure 2:
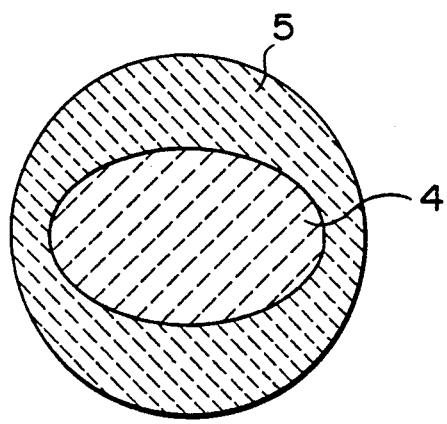
FIG. 2 is a sectional view showing a sustained release material as a modification of the first embodiment.

As a modification of the above first embodiment, a sustained release material having the arrangement as shown in FIG. 2 will be proposed. This sustained release material is formed into a spherical shape as a whole. An elliptic porous core 4 having a high porosity is arranged at the central portion of the sphere, and a spherical surface layer 5 having a low porosity is formed around the core 4.

According to the modification of the sustained release material having the above arrangement, different diffusion/release rates can be effectively obtained in the vertical and horizontal directions of the sustained release material due to the shape as described above.

The second embodiment of the present invention will be described below.

Figure 3:
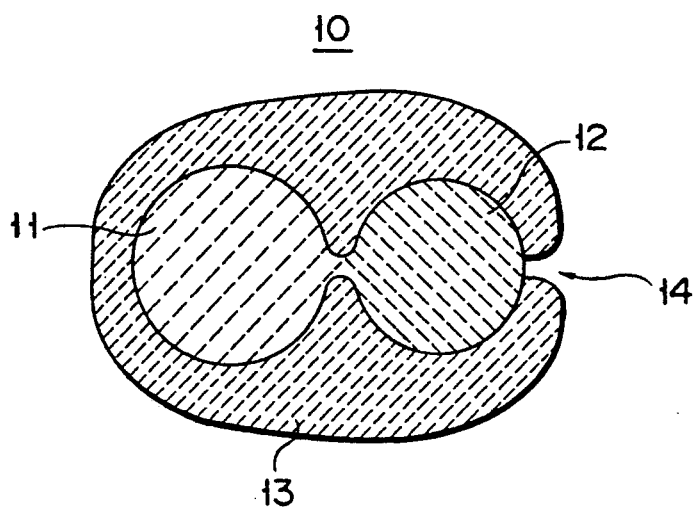
FIG. 3 is a sectional view showing a sustained release material according to the second embodiment of the present invention.

FIG. 3 is a sectional view showing a sustained release material according to the second embodiment. In this sustained release material 10, a first spherical porous core 11 having a porosity of 60% is bonded to a second spherical porous core 12 having a porosity of 30%, and a surface layer 13 consisting of a dense material is formed around this bonded body. A communication path 14 for allowing the second core 12 to communicate with the exterior is formed in the dense surface layer 13. This communication path 14 serves as a release port for slowly releasing a liquid drug moved from the first core 11 to the second core 12 to outside the sustained release material.

A method of manufacturing the sustained release material 10 having the above arrangement will be described below.

As a base material constituting the sustained release material 10, $\beta$-TCP having high affinity to a living body is used as in the first embodiment.

2.7 ml of a foaming agent, 8 ml of a foam stabilizer, and 15 ml of water are added to 30 g of $\beta$-TCP synthesized by the mechanochemical method, and the resultant material is mixed under stirring, thereby preparing a high-porosity foaming slurry having a porosity of 60%.

In addition, 2 ml of a foaming agent, 5 ml of a foam stabilizer, and 10 ml of water are added to 30 g of $\beta$-TCP, and the resultant material is mixed to prepare a low-porosity foaming slurry having a porosity of 30%.

The high-porosity foaming slurry is subjected to casting using a silicone rubber mold having a spherical shape as a whole and a diameter of 5 mm, and the low-porosity foaming slurry is subjected to casting using another silicone rubber mold having a spherical shape as a whole and a diameter of 4 mm. After spherical molded bodies formed by the two casting processes are dried, the two spherical molded bodies are bonded to each other by a using a wax. Thereafter, the distal end of a stick wax is adhered to a predetermined portion of the spherical molded body consisting of the low-porosity foaming slurry.

In a separate step, 10 ml of a 10% aqueous defloccu-lant solution are added to 20 g of $\beta$-TCP, and the resultant material is mixed to prepare a dense slurry.

The bonded body formed as described above is dipped in the dense slurry while being supported by the stick of wax and then pulled up and dried. Thereafter, the stick wax is removed, and the resultant material is sintered at 1,100° C. for one hour. As a result, the bonded body of the spherical molded bodies is covered with a dense surface layer 13 consisting of the sintered dense slurry, and a portion where the stick wax was present remains empty as the communication path 14.

As in the first embodiment described above, a liquid drug is impregnated in the obtained sustained release material 10 at a reduced pressure. A release rate of the liquid drug obtained when the sustained release material is buried in a diseased part depends on the size of the communication path 14 and the diffusion amount of the liquid drug from the low-porosity second core 12. The impregnation amount is determined by the high-porosity first core 11.

According to the second embodiment as described above, since the sustained release time is controlled by the size of the communication path 14 and the diffusion amount of a liquid drug from the low-porosity second core 12 on the release port side, slow release can be performed over a longer time period than that in the first embodiment.

The third embodiment of the present invention will be described below.

Figure 4:
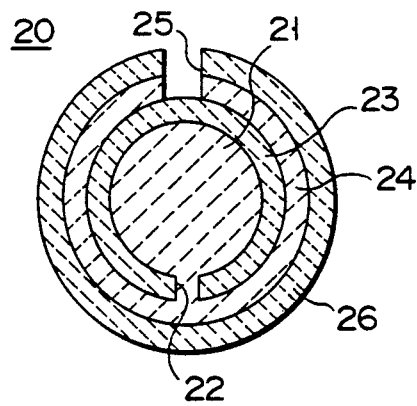
FIG. 4 is a sectional view showing a sustained release material according to the third embodiment of the present invention.

FIG. 4 is a sectional view showing a sustained release material according to the third embodiment of the present invention. A sustained release material 20 according to this embodiment is constituted by a spherical ceramic as a whole. A porous core 21 into which a liquid drug is to be impregnated is arranged at the central portion of the section of the sustained release material 20, and a dense first interlayer 23 having a first communication path 22 therein is formed around the core 21. A porous second interlayer 24 having a liquid drug absorbing function similar to that of the core 21 is formed around the first interlayer 23. In addition, a dense surface layer 26 having a second communication path 25 formed in a position different from that of the first communication path 22 is formed around the second interlayer 24.

A method of manufacturing the sustained release material 20 having the above arrangement will be described below with reference to FIGS. 5A to 5E.

In this embodiment, $\beta$-TCP is used as a base material.

2.7 ml of a foaming agent, 6 ml of a foam stabilizer, and 12 ml of water are added to 30 g of a $\beta$-TCP powder synthesized by the mechanochemical method, and the resultant material is mixed under stirring, thereby preparing a foaming slurry. In addition, 10 ml of a 10% aqueous deflocculant solution are added to 20 g of a $\beta$-TCP powder synthesized by the mechanochemical method, and the resultant material is mixed to prepare a dense slurry.

Figure 5A:
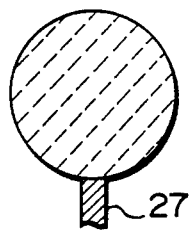
FIG. 5A is a view showing a first step of a method of manufacturing the sustained release material according to the third embodiment.
Figure 5B:
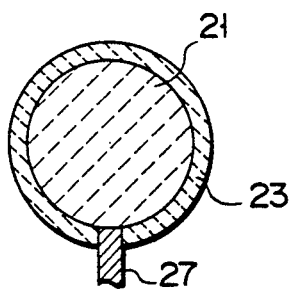
FIG. 5B is a view showing a second step of the method of manufacturing the sustained release material according to the third embodiment.

The above foaming slurry is cast in a silicone rubber mold capable of forming a spherical molded body having a diameter of 5 mm and removed from the mold after being dried. As a result, a porous core 21 is molded. Thereafter, as shown in FIG. 5A, the distal end of a stick wax 27 having a diameter of 1 mm is heated and adhered to a predetermined portion of the core 21. The other end of the stick wax 27 is held to dip the core 21 in the above dense slurry and immediately pulled up therefrom, thereby coating the dense slurry around the core 21, as shown in FIG. 5B. After the resultant structure is dried, the stick wax 27 is removed. As a result, the dense slurry serves as a first interlayer 23, and a portion of the first interlayer 23, from which the wax 27 is removed, remains as a first communication path 22.

Figure 5C:
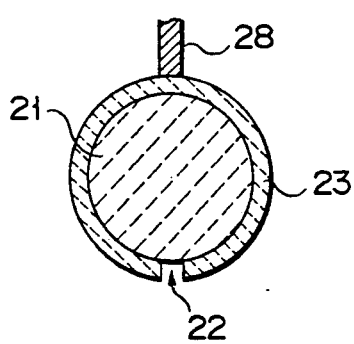
FIG. 5C is a view showing a third step of the method of manufacturing the sustained release material according to the third embodiment.
Figure 5D:
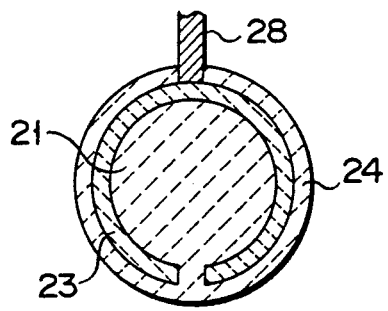
FIG. 5D is a view showing a fourth step of the method of manufacturing the sustained release material according to the third embodiment.

As shown in FIG. 5C, the distal end of a stick wax 28 is adhered to a predetermined portion of the first interlayer 23 on a side opposite to the formation position of the first communication path 22. The other end of the stick wax 28 is held to dip the first interlayer 23 in the above foaming slurry and immediately pulled up therefrom, thereby coating the foaming slurry around the first interlayer 23, as shown in FIG. 5D. The resultant structure is dried to coat the adhered foaming slurry as a second porous interlayer 24.

Figure 5E:
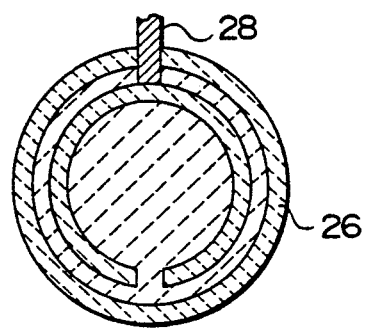
FIG. 5E is a view showing a fifth step of the method of manufacturing the sustained release material according to the third embodiment.

The other end portion of the stick wax 28 is held again to dip the second interlayer 24 in the above dense slurry to coat the dense slurry around the second interlayer 24, as shown in FIG. 5E. The resultant structure is dried to form a dense surface layer 26.

The entire structure is sintered at 1,100° C. for one hour to melt the wax sticks 27 and 28 to form first and second communication paths 22 and 25 in the corresponding portions, respectively. When the slurry is sintered, the sustained release material shown in FIG. 4 is formed.

The formed sustained release material is left to stand in a liquid drug to impregnate the drug.

According to the sustained release material 20 manufactured as described above, the drug impregnated in the core 21 located in the central portion of the sustained release material is moved to the second interlayer 24 through the first communication path 22 formed in the first interlayer 23 and diffused and released to outside from the second communication path 25 in the surface layer 26. Since the first and second communication paths 22 and 25 are partitioned stepwise by the dense first interlayer 23 and the dense surface layer 26, a release amount of the liquid drug is suppressed to realize a long release time as compared with the sustained release material consisting of only a porous material. Therefore, since sustained release can be performed over a long time period, a conspicuous therapeutic effect that cannot be obtained by conventional sustained release materials can be obtained.

In addition, since $\beta$-TCP is used as a base material, especially when the sustained release material of this embodiment is buried in a bone tissue to cure osteomyelitis or the like, the base material is bonded to the bone to form a new bone after release of a drug is finished.

Figure 6:
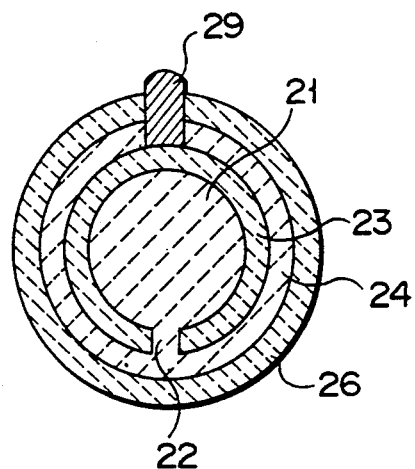
FIG. 6 is a sectional view showing a state in which a communication path of the sustained release material according to the third embodiment is closed by a vital cement.

Note that in the above embodiment, when the second communication path 25 in the surface layer 26 is closed by a vital cement 29 as shown in FIG. 6 after a liquid drug is impregnated, a sustained release time of the liquid drug can be further prolonged. In addition, release of the liquid drug during storage can be suppressed.

The above embodiment has been described by taking $\beta$-TCP as an example of the base material. However, the same effect as the above embodiment can be obtained by using another ceramic having affinity to a living body such as apatite hydroxide, a composite body of $\beta$-TCP and apatite hydroxide, calcium phosphate, alumina, or zirconia.

The fourth embodiment of the present invention will be described below with reference to FIGS. 7A, 7B, and 8.

Figure 7A:
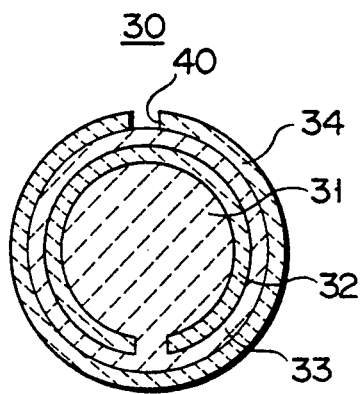
FIG. 7A is a longitudinal sectional view showing a sustained release material according to the fourth embodiment of the present invention.
Figure 7B:
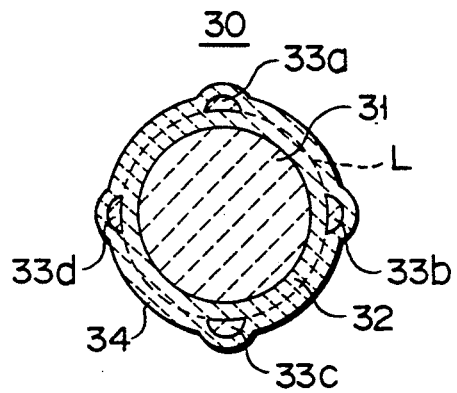
FIG. 7B is a cross-sectional view showing the sustained release material of the fourth embodiment.
Figure 8:
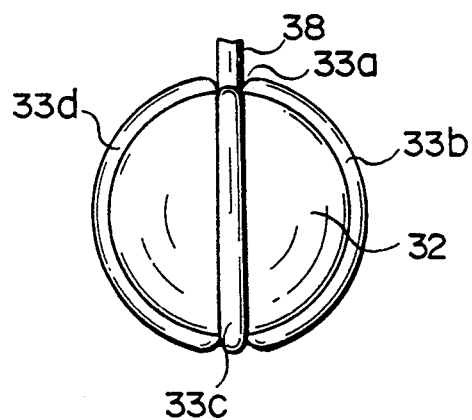
FIG. 8 is a view showing a main step of a method of manufacturing the sustained release material of the fourth embodiment.

FIGS. 7A and 7B are sectional views showing the section in the longitudinal direction (A) and that in the transverse direction (B) of a sustained release material according to this embodiment.

In this sustained release material 30, a porous core 31 is formed in the central portion, and a dense interlayer 32 is formed around the core 31 to a region indicated by a dotted line L in FIG. 7B. A plurality of porous projections 33a to 33d are formed on the surface of the interlayer 32. In addition, a dense surface layer 34 is formed on the surface of the entire structure.

A main part of a manufacturing method of this embodiment will be described below. As shown in FIG. 8, the distal end of a stick wax 38 is adhered on a position at which the plurality of projections 33a to 33d are gathered. The other end of the stick wax 38 is held to dip the resultant structure in a dense slurry to form a dense surface layer 34. The stick wax 38 is removed to form a communication path 40 for allowing the projections 33a to 33d to communicate with the exterior.

Note that the core 31 and the interlayer 32 have a communication path 41 formed in the same manner as the above embodiment.

In this embodiment, the porous layer interposed between the dense interlayer 32 and the dense surface layer 34 is not formed on the entire surface of the sphere but formed on only a part thereof.

Since an impregnated liquid drug is released from the core 31 through the projections 33a to 33d, the liquid drug is released less than in the above embodiments to realize longer slow release.

Additional advantages and modifications will readily occur to those skilled in the art. Therefore, the invention in its broader aspects is not limited to the specific details, representative devices, and illustrated examples shown and described herein. Accordingly, various modifications may be made without departing from the spirit or scope of the general inventive concept as defined by the appended claims and their equivalents.

What is claimed is:

1. A sustained release material to be buried at a position close to a diseased part in a living body to slowly release an impregnated liquid drug, comprising:
   a porous core into which said liquid drug is impregnated;
   a dense first interlayer formed around said core;
   a porous portion formed around said first interlayer;
   a dense surface layer formed to cover said first interlayer and said porous portion;
   a first communication path for allowing sad porous core to communicate with said porous portion; and
   a second communication path for allowing said porous portion to communicate with the exterior.

2. A sustained release material according to claim 1, wherein said porous portion comprises a second interlayer formed around said first interlayer.

3. A sustained release material according to claim 2, wherein said second communication path further allows said first interlayer to communicate with the exterior.

4. A sustained release material according to claim 2, wherein each of said core, said first and second interlayers, and said surface layer consists of a material selected from the group consisting of β-tricalcium phosphate, apatite hydroxide, a composite body of β-tricalcium phosphate and apatite hydroxide, calcium phosphate, alumina, and zirconia.

5. A sustained release material according to claim 1, wherein said porous portion comprises a plurality of porous projections formed around said first interlayer.

* * * * *